US012686879B2

(12) United States Patent
Appeldoorn et al.

(10) Patent No.: US 12,686,879 B2
(45) Date of Patent: Jul. 21, 2026

(54) PROCESS FOR THE PREPARATION OF A SUGAR PRODUCT AND A FERMENTATION PRODUCT

(71) Applicant: VERSALIS S.P.A., San Donato Milanese (IT)

(72) Inventors: Maaike Appeldoorn, San Donato Milanese (IT); Bertus Noordam, San Donato Milanese (IT)

(73) Assignee: VERSALIS S.P.A., San Donato Milanese (IT)

( * ) Notice: Subject to any disclaimer, the term of this patent is extended or adjusted under 35 U.S.C. 154(b) by 338 days.

(21) Appl. No.: 18/553,977

(22) PCT Filed: Apr. 5, 2022

(86) PCT No.: PCT/EP2022/058941
§ 371 (c)(1),
(2) Date: Oct. 4, 2023

(87) PCT Pub. No.: WO2022/214460
PCT Pub. Date: Oct. 13, 2022

(65) Prior Publication Data
US 2024/0182938 A1     Jun. 6, 2024

(30) Foreign Application Priority Data
Apr. 8, 2021    (EP) .................................... 21167451

(51) Int. Cl.
*C12P 19/04*        (2006.01)
*C12P 19/14*        (2006.01)
(52) U.S. Cl.
CPC .............. *C12P 19/04* (2013.01); *C12P 19/14* (2013.01); *C12P 2203/00* (2013.01)
(58) Field of Classification Search
None
See application file for complete search history.

(56) References Cited

U.S. PATENT DOCUMENTS

| | | | |
|---|---|---|---|
| 5,275,944 A | 1/1994 | Himmel et al. | |
| 5,457,046 A | 10/1995 | Wöldike et al. | |
| 5,536,655 A | 7/1996 | Thomas et al. | |
| 5,648,263 A | 7/1997 | Schülein et al. | |
| 5,686,593 A | 11/1997 | Wöldike et al. | |
| 6,022,725 A | 2/2000 | Fowler et al. | |
| 6,982,159 B2 | 1/2006 | Dunn-Coleman et al. | |
| 7,005,289 B2 | 2/2006 | Dunn-Coleman et al. | |
| 7,045,332 B2 | 5/2006 | Dunn-Coleman et al. | |
| 2004/0102619 A1 | 5/2004 | Dunn-Coleman et al. | |
| 2006/0258554 A1 | 11/2006 | Dunn-Coleman et al. | |
| 2015/0299749 A1* | 10/2015 | Noordam ................ | C12P 19/02 435/165 |
| 2017/0044584 A1 | 2/2017 | Noordam | |
| 2017/0183698 A1 | 6/2017 | Noordam | |
| 2017/0247722 A1* | 8/2017 | Smits ..................... | C13K 13/00 |
| 2018/0073048 A1* | 3/2018 | Noordam ................ | C12P 19/14 |

FOREIGN PATENT DOCUMENTS

| | | |
|---|---|---|
| EA | 031865 B1 | 3/2019 |
| EA | 035176 B1 | 5/2020 |
| EP | 1 499 708 B2 | 2/2012 |
| EP | 1 468 093 B2 | 1/2018 |
| WO | 91/05039 A1 | 4/1991 |
| WO | 93/15186 A1 | 8/1993 |
| WO | 94/21785 A1 | 9/1994 |
| WO | 96/02551 A1 | 2/1996 |
| WO | 98/13465 A1 | 4/1998 |
| WO | 98/15619 A1 | 4/1998 |
| WO | 98/15633 A1 | 4/1998 |
| WO | 99/06574 A1 | 2/1999 |
| WO | 99/10481 A2 | 3/1999 |
| WO | 99/25847 A2 | 5/1999 |
| WO | 99/31255 A2 | 6/1999 |
| WO | 00/70031 A1 | 11/2000 |
| WO | 02/24926 A1 | 3/2002 |
| WO | 02/095014 A2 | 11/2002 |
| WO | 02/10178 A2 | 12/2002 |
| WO | 03/027306 A2 | 4/2003 |
| WO | 03/052054 A2 | 6/2003 |
| WO | 03/052055 A2 | 6/2003 |
| WO | 03/052056 A2 | 6/2003 |
| WO | 03/052057 A2 | 6/2003 |
| WO | 03/052118 A2 | 6/2003 |
| WO | 03/095627 A1 | 11/2003 |
| WO | 2004/016760 A2 | 2/2004 |
| WO | 2004/043980 A2 | 5/2004 |
| WO | 2004/048592 A2 | 6/2004 |
| WO | 2005/001036 A2 | 1/2005 |
| WO | 2005/001065 A2 | 1/2005 |
| WO | 2005/028636 A2 | 3/2005 |
| WO | 2005/047499 A1 | 5/2005 |
| WO | 2005/074647 A2 | 8/2005 |
| WO | 2005/074656 A2 | 8/2005 |
| WO | 2005/093050 A2 | 10/2005 |
| WO | 2005/093050 A3 | 10/2005 |
| WO | 2005/093073 A1 | 10/2005 |
| WO | 2006/009434 A1 | 1/2006 |
| WO | 2006/074005 A2 | 7/2006 |
| WO | 2006/078256 A2 | 7/2006 |

(Continued)

OTHER PUBLICATIONS

Foreman et al.; "Transcriptional Regulation of Biomass-degrading Enzymes in the Filamentous Fungus *Trichoderma reesei*"; Jun. 4, 2003, The Journal of Biological Chemistry, vol. 278 , No. 34, Issue of Aug. 22, pp. 31988-31997k.
Isaksen et al.; "A C4-oxidizing Lytic Polysaccharide Monooxygenase Cleaving Both Cellulose and Cello-oligosaccharides"; Journal of Biological Chemistry, Dec. 2013, pp. 2632-2642.
International Search Report dated Jul. 15, 2022 from corresponding International Patent Application No. PCT/EP2022/058941, 3 pages.
Written Opinion dated Jul. 15, 2022 from corresponding International Patent Application No. PCT/EP2022/058941, 7 pages.

*Primary Examiner* — Blaine Lankford
(74) *Attorney, Agent, or Firm* — Ruggiero McAllister & McMahon LLC

(57) ABSTRACT

There is a process for the preparation of a sugar product from cellulosic material and a process for the preparation of a fermentation product from cellulosic material.

13 Claims, No Drawings

(56)     References Cited

FOREIGN PATENT DOCUMENTS

| WO | 2006/114094 | A1 | 11/2006 |
| WO | 2006/117432 | A1 | 11/2006 |
| WO | 2007/019442 | A2 | 2/2007 |
| WO | 2007/071818 | A1 | 6/2007 |
| WO | 2007/071820 | A1 | 6/2007 |
| WO | 2007/089290 | A2 | 8/2007 |
| WO | 2008/008070 | A2 | 1/2008 |
| WO | 2008/041840 | A1 | 4/2008 |
| WO | 2008/057637 | A2 | 5/2008 |
| WO | 2008/148131 | A1 | 12/2008 |
| WO | 2009/011591 | A2 | 1/2009 |
| WO | 2009/042846 | A1 | 4/2009 |
| WO | 2009/068565 | A1 | 6/2009 |
| WO | 2009/073383 | A1 | 6/2009 |
| WO | 2009/073709 | A1 | 6/2009 |
| WO | 2009/076122 | A1 | 6/2009 |
| WO | 2009/079210 | A2 | 6/2009 |
| WO | 2009/085859 | A2 | 7/2009 |
| WO | 2009/085864 | A2 | 7/2009 |
| WO | 2009/085868 | A1 | 7/2009 |
| WO | 2009/085935 | A2 | 7/2009 |
| WO | 2009/127729 | A1 | 10/2009 |
| WO | 2010/000888 | A1 | 1/2010 |
| WO | 2010/014706 | A1 | 2/2010 |
| WO | 2010/014880 | A1 | 2/2010 |
| WO | 2010/053838 | A1 | 5/2010 |
| WO | 2010/065448 | A1 | 6/2010 |
| WO | 2010/065830 | A1 | 6/2010 |
| WO | 2010/108918 | A1 | 9/2010 |
| WO | 2010/122141 | A1 | 10/2010 |
| WO | 2010/126772 | A1 | 11/2010 |
| WO | 2010/138754 | A1 | 12/2010 |
| WO | 2011/005867 | A1 | 1/2011 |
| WO | 2011/035027 | A2 | 3/2011 |
| WO | 2011/035029 | A1 | 3/2011 |
| WO | 2011/039319 | A1 | 4/2011 |
| WO | 2011/041397 | A1 | 4/2011 |
| WO | 2011/041405 | A1 | 4/2011 |
| WO | 2011/041504 | A1 | 4/2011 |
| WO | 2011/057083 | A1 | 5/2011 |
| WO | 2011/057140 | A1 | 5/2011 |
| WO | 2011/098580 | A1 | 8/2011 |
| WO | 2012/000886 | A1 | 1/2012 |
| WO | 2012/000890 | A1 | 1/2012 |
| WO | 2012/000892 | A1 | 1/2012 |
| WO | 2012/044915 | A2 | 4/2012 |
| WO | 2013/028928 | A1 | 2/2013 |
| WO | 2014/118360 | A2 | 8/2014 |
| WO | 2014/130812 | A1 | 8/2014 |
| WO | 2015/081139 | A1 | 6/2015 |
| WO | 2015/165951 | A1 | 11/2015 |
| WO | 2015/187935 | A1 | 12/2015 |
| WO | 2016/082771 | A1 | 6/2016 |

* cited by examiner

PROCESS FOR THE PREPARATION OF A SUGAR PRODUCT AND A FERMENTATION PRODUCT

CROSS-REFERENCE TO A RELATED APPLICATIONS

The present application claims priority based on PCT/EP2022/058941, filed Apr. 5, 2022, which claims priority based on European Application No. 21167451.0, filed Apr. 8, 2021, both of which are incorporated herein in their entireties.

FIELD OF THE DISCLOSURE

The application relates to a process for the preparation of a sugar product from cellulosic material and a process for the preparation of a fermentation product from cellulosic material.

DESCRIPTION OF THE RELATED ART

Cellulosic material is primarily composed of cellulose and may also comprise hemicellulose and lignin. It provides an attractive platform for generating alternative energy sources to fossil fuels. The material is available in large amounts and can be converted into valuable products e.g. sugars or biofuel, such as bioethanol.

Producing fermentation products from cellulosic material is known in the art and generally includes the steps of pretreatment, hydrolysis, fermentation, and optionally recovery of the fermentation products.

Commonly, the sugars produced are converted into valuable fermentation products such as ethanol by microorganisms like yeast. The fermentation takes place in a separate, preferably anaerobic, process step, either in the same or in a different vessel.

In general, cost of enzyme production is a major cost factor in the overall production process of fermentation products from cellulosic material. Thus far, reduction of enzyme production costs is achieved by applying enzyme products from a single or from multiple microbial sources (see WO 2008/008793) with broader and/or higher (specific) hydrolytic activity. This leads to a lower enzyme need, faster conversion rates and/or higher conversion yields and thus to lower overall production costs.

Next to the optimization of enzymes, optimization of process design is a crucial tool to reduce overall costs of the production of sugar products and fermentation products. For example, sugar loss by means of sugar degradation products increases with decreasing yield. Since sugar degradation products can inhibit fermentation, process design should be optimized to decrease the amount of these sugar degradation products.

For economic reasons, it is therefore desirable to include new and innovative process configurations aimed at reducing overall production costs in the process involving pretreatment, hydrolysis and fermentation of cellulosic material.

SUMMARY OF THE DISCLOSURE

An object of the application is to provide an improved process for the preparation of a sugar product from cellulosic material and an improved process for the preparation of a fermentation product from cellulosic material. The processes are improved by using specific hydrolysis conditions.

DETAILED DESCRIPTION OF THE DISCLOSURE

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The present disclosure relates to a process for the preparation of a sugar product from cellulosic material, comprising the following steps (a) enzymatic hydrolysis of the cellulosic material using an enzyme composition to obtain a sugar product, wherein oxygen is added during at least part of the enzymatic hydrolysis in an amount that xylonic acid is formed in an amount of 500 to 1100 μmol xylonic acid/kg xylan in the cellulosic material per hour, and (b) optionally, recovery of the sugar product.

The present disclosure also relates to a process for the preparation of a fermentation product from cellulosic material, comprising the following steps (a) enzymatic hydrolysis of the cellulosic material using an enzyme composition to obtain a sugar product, wherein oxygen is added during at least part of the enzymatic hydrolysis in an amount that xylonic acid is formed in an amount of 500 to 1100 μmol xylonic acid/kg xylan in the cellulosic material per hour, (b) fermentation of the hydrolysed cellulosic material to produce a fermentation product, and (c) optionally, recovery of the fermentation product.

After enzymatic hydrolysis, the hydrolysed cellulosic material may be subjected to at least one solid/liquid separation. The methods and conditions of solid/liquid separation will depend on the type of cellulosic material used and are well within the scope of the skilled artisan. Examples include, but are not limited to, centrifugation, cyclonic separation, filtration, decantation, sieving and sedimentation. In a preferred embodiment the solid/liquid separation is performed by centrifugation or sedimentation. During solid/liquid separation, means and/or aids for improving the separation may be used.

In an embodiment the cellulosic material is subjected to a pretreatment step before the enzymatic hydrolysis. In other words, in an embodiment the cellulosic material is pretreated before enzymatic hydrolysis. Different pretreatment methods are described below.

In an embodiment the cellulosic material is subjected to a washing step before the enzymatic hydrolysis. In an embodiment the cellulosic material is subjected to at least one solid/liquid separation before the enzymatic hydrolysis. So, before subjecting the cellulosic material to enzymatic hydrolysis, it can be subjected to at least one solid/liquid separation. The solid/liquid separation may be done before and/or after the pretreatment step. Suitable methods and conditions for a solid/liquid separation have been described above.

In an embodiment the enzymatically hydrolysed cellulosic material is subjected to a solid/liquid separation step followed by a detoxification step and/or a concentration step.

In the processes as described herein cellulosic material may be added to the one or more hydrolysis reactors. In an embodiment the enzyme composition is already present in the one or more hydrolysis reactors before the cellulosic material is added. In another embodiment the enzyme composition may be added to the one or more hydrolysis reactors. In an embodiment the cellulosic material is already present in the one or more hydrolysis reactors before the enzyme composition is added. In an embodiment both the cellulosic material and the enzyme composition are added simultaneously to the one or more hydrolysis reactors. The enzyme composition present in the one or more hydrolysis reactors may be an aqueous composition.

In an embodiment the enzymatic hydrolysis comprises at least a liquefaction step wherein the cellulosic material is hydrolysed in at least a first hydrolysis reactor, and a saccharification step wherein the liquefied cellulosic material is hydrolysed in the at least first hydrolysis reactor and/or in at least a second hydrolysis reactor. Saccharification can be done in the same hydrolysis reactor as the liquefaction (i.e. the at least first hydrolysis reactor), it can also be done in a separate hydrolysis reactor (i.e. the at least second hydrolysis reactor). So, in the enzymatic hydrolysis liquefaction and saccharification may be combined. Alternatively, the liquefaction and saccharification may be separate steps. Liquefaction and saccharification may be performed at different temperatures but may also be performed at a single temperature. In an embodiment the temperature of the liquefaction is higher than the temperature of the saccharification. Liquefaction is preferably carried out at a temperature of 60-85° C. and saccharification is preferably carried out at a temperature of 50-65° C.

The enzymatic hydrolysis can be performed in one or more hydrolysis reactors but can also be performed in one or more tubes or any other continuous system. This also holds true when the enzymatic hydrolysis comprises a liquefaction step and a saccharification step. The liquefaction step can be performed in one or more hydrolysis reactors but can also be performed in one or more tubes or any other continuous system and/or the saccharification step can be performed in one or more hydrolysis reactors, but can also be performed in one or more tubes or any other continuous system. In an embodiment the enzymatic hydrolysis takes place in a batch, fed batch and/or continuous culture reactor. Examples of hydrolysis reactors to be used include, but are not limited to, fed-batch stirred reactors, batch stirred reactors, continuous flow stirred reactors with ultrafiltration, and continuous plug-flow column reactors. Stirring can be done by one or more impellers, pumps and/or static mixers.

The enzymes used in the enzymatic hydrolysis may be added before and/or during the enzymatic hydrolysis. As indicated above, when the cellulosic material is subjected to a solid/liquid separation before enzymatic hydrolysis, the enzymes used in the enzymatic hydrolysis may be added before the solid/liquid separation. Alternatively, they may also be added after solid/liquid separation or before and after solid/liquid separation. The enzymes may also be added during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total enzymatic hydrolysis time is 10 to 300 hours, 16 to 275 hours, preferably 20 to 250 hours, more preferably 30 to 200 hours, most preferably 40 to 150 hours.

The viscosity of the cellulosic material in the one or more hydrolysis reactors used for the enzymatic hydrolysis is between 10 and 20,000 cP, between 10 and 15,000 cP, preferably between 10 and 10,000 cP.

In case the process comprises an enzymatic hydrolysis comprising a liquefaction step and a saccharification step, the viscosity of the cellulosic material in the liquefaction step is between 10 and 4000 cP, between 10 and 2000 cP, preferably between 10 and 1000 cP and/or the viscosity of the cellulosic material in the saccharification step is preferably between 10 and 1000 cP.

The viscosity can be determined with a Rheolab QC viscosity meter using a Rushton impellor at the temperature used for the hydrolysis and at a Reynolds number <10.

Oxygen is added during at least part of the enzymatic hydrolysis. In an embodiment oxygen is added during the whole enzymatic hydrolysis. Oxygen can be added continuously or discontinuously during the enzymatic hydrolysis. In an embodiment oxygen is added one or more times during the enzymatic hydrolysis. Oxygen may also be added before the enzymatic hydrolysis, during the addition of cellulosic material to a hydrolysis reactor used for enzymatic hydrolysis, during the addition of enzyme to a hydrolysis reactor used for enzymatic hydrolysis or any combination thereof. Oxygen is added to the one or more hydrolysis reactors used in the enzymatic hydrolysis.

Oxygen can be added in several forms. For example, oxygen can be added as oxygen gas, oxygen-enriched gas, such as oxygen-enriched air, or air. Examples how to add oxygen include, but are not limited to, addition of oxygen by means of sparging, electrolysis, chemical addition of oxygen, filling the one or more hydrolysis reactors used in the enzymatic hydrolysis from the top (plunging the hydrolysate into the tank and consequently introducing oxygen into the hydrolysate) and addition of oxygen to the headspace of said one or more hydrolysis reactors. When oxygen is added to the headspace of the hydrolysis reactor(s), sufficient oxygen necessary for the hydrolysis reaction may be supplied in case small hydrolysis reactors (i.e. <1 m³) are used. When big, i.e. commercial, hydrolysis reactors (i.e. >1 m³) are used, addition of oxygen via the headspace is insufficient and oxygen will need to be added by, for example, sparging or blowing oxygen into the cellulosic material. In general, the amount of oxygen added to the hydrolysis reactor(s) can be controlled and/or varied. Restriction of the oxygen supplied is possible by adding only oxygen during part of the hydrolysis time in said hydrolysis reactor(s). Another option is adding oxygen at a low concentration, for example by using a mixture of air and recycled air (air leaving the hydrolysis reactor) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen concentration during enzymatic hydrolysis of the cellulosic material can be measured, for example by using a DO (dissolved oxygen) electrode.

In an embodiment oxygen is added to the one or more hydrolysis reactors used in the enzymatic hydrolysis before and/or during and/or after the addition of the cellulosic material to said one or more hydrolysis reactors. The oxygen may be introduced together with the cellulosic material that enters the hydrolysis reactor(s). The oxygen may be introduced into the material stream that will enter the hydrolysis reactor(s) or with part of the hydrolysis reactor(s) contents that passes an external loop of the hydrolysis reactor(s).

Oxygen is added during at least part of the enzymatic hydrolysis in an amount that xylonic acid is formed in an amount of 500 to 1100 µmol xylonic acid/kg xylan in the cellulosic material per hour. In a preferred embodiment oxygen is added during at least part of the enzymatic hydrolysis in an amount that xylonic acid is formed in an amount of 510 to 1090 µmol xylonic acid/kg xylan in the cellulosic material per hour. In a more preferred embodiment oxygen is added during at least part of the enzymatic hydrolysis in an amount that xylonic acid is formed in an amount of 520 to 1080 µmol xylonic acid/kg xylan in the cellulosic material per hour. In an even more preferred embodiment oxygen is added during at least part of the enzymatic hydrolysis in an amount that xylonic acid is formed in an amount of 530 to 1070 µmol xylonic acid/kg xylan in the cellulosic material per hour. In the most preferred embodiment oxygen is added during at least part of the enzymatic hydrolysis in an amount that xylonic acid is formed in an amount of 540 to 1050 µmol xylonic acid/kg xylan in the cellulosic material per hour.

In an embodiment oxygen is added to maintain an oxygen concentration of 0.0002-0.047 mol $O_2/m^3$ during enzymatic hydrolysis. In a preferred embodiment oxygen is added to maintain an oxygen concentration of 0.0002-0.002 mol $O_2/m^3$ during enzymatic hydrolysis. In a preferred embodiment oxygen is added to maintain an oxygen concentration of 0.002-0.016 mol $O_2/m^3$ during enzymatic hydrolysis. In a preferred embodiment oxygen is added to maintain an oxygen concentration of 0.016-0.047 mol $O_2/m^3$ during enzymatic hydrolysis. The "mol $O_2/m^3$" values given above relate to values measured at normal atmospheric pressure and a temperature of 60° C. The values will differ when a different pressure and/or temperature is used. It is well within the reach of a person skilled in the art to calculate the "mol $O_2/m^3$" values when a different pressure and/or temperature is used.

In an embodiment the reactor(s) used in the enzymatic hydrolysis and/or the fermentation have a volume of at least 1 $m^3$. Preferably, the reactors have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the reactor(s) will be smaller than 3000 $m^3$ or 5000 $m^3$. In case several reactors are used in the enzymatic hydrolysis, they may have the same volume, but also may have a different volume. In case the enzymatic hydrolysis comprises a separate liquefaction step and saccharification step, the hydrolysis reactor(s) used for the liquefaction step and the hydrolysis reactor(s) used for the saccharification step may have the same volume, but also may have a different volume.

In an embodiment the enzymatic hydrolysis is done at a temperature of 40-90° C., preferably 45-80° C., more preferably 50-70° C. and most preferably 55-65° C.

Cellulosic material as used herein includes any cellulose containing material. Preferably, cellulosic material as used herein includes lignocellulosic and/or hemicellulosic material. Cellulosic material as used herein may also comprise starch and/or sucrose. Cellulosic material suitable for use in the processes as described herein includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, rye, oat, wheat straw, sugar cane, cane straw, sugar cane bagasse, switch grass, miscanthus, energy cane, cassava, molasse, barley, corn, corn stover, corn fiber, corn husks, corn cobs, canola stems, soybean stems, sweet sorghum, corn kernel including fiber from kernels, distillers dried grains (DDGS), products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

In an embodiment the cellulosic material is pretreated before the enzymatic hydrolysis. Pretreatment methods are known in the art and include, but are not limited to, heat, mechanical, chemical modification, biological modification and any combination thereof. In an embodiment the pretreatment is steam treatment, dilute acid treatment, organosolv treatment, lime treatment, ARP treatment or AFEX treatment. Pretreatment is typically performed in order to enhance the accessibility of the cellulosic material to enzymatic hydrolysis and/or hydrolyse the hemicellulose and/or solubilize the hemicellulose and/or cellulose and/or lignin, in the cellulosic material. In an embodiment, the pretreatment comprises treating the cellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g.

treatment with >15% NH$_3$, at 60-140° C., at a pressure of 8-20 bar, at alkaline pH, for 5-30 minutes).

The cellulosic material may be washed. In an embodiment the cellulosic material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The cellulosic material may also be detoxified by any (or any combination) of these methods which include, but are not limited to, solid/liquid separation, vacuum evaporation, extraction, adsorption, neutralization, over liming, addition of reducing agents, addition of detoxifying enzymes such as laccases or peroxidases, addition of microorganisms capable of detoxification of hydrolysates.

In an embodiment the hydrolysis step is conducted until 70% or more, 80% or more, 85% or more, 90% or more, 92% or more, 95% or more of available sugar in the cellulosic material is released.

In an embodiment the dry matter content of the cellulosic material in the enzymatic hydrolysis is from 10%-40% (w/w), 11%-35% (w/w), 12%-30% (w/w), 13%-29% (w/w), 14%-28% (w/w), 15%-27% (w/w), 16%-26% (w/w), 17%-25% (w/w).

In an embodiment the amount of enzyme composition added (herein also called enzyme dosage or enzyme load) in the hydrolysis is low. In an embodiment the amount of enzyme composition is 10 mg protein/g dry matter weight or lower, 9 mg protein/g dry matter weight or lower, 8 mg protein/g dry matter weight or lower, 7 mg protein/g dry matter weight or lower, 6 mg protein/g dry matter weight or lower, 5 mg protein/g dry matter or lower, 4 mg protein/g dry matter or lower, 3 mg protein/g dry matter or lower, 2.5 mg protein/g dry matter or lower, 2 mg protein/g dry matter or lower, or 1 mg protein/g dry matter or lower (expressed as protein in mg protein/g dry matter). Obviously, the amount of enzyme composition is more than 0. In an embodiment, the amount of enzyme composition is 5 mg enzyme/g dry matter weight or lower, 4 mg enzyme/g dry matter weight or lower, 3 mg enzyme/g dry matter weight or lower, 2.5 mg protein/g dry matter or lower, 2 mg enzyme/g dry matter weight or lower, 1 mg enzyme/g dry matter weight or lower, 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). Obviously, the amount of enzyme is more than 0.

In an embodiment the enzyme composition is used in the enzymatic hydrolysis in an amount of 1 mg to 20 mg protein/gram dry matter weight of glucans in the cellulosic material. In an embodiment the enzyme composition is used in the enzymatic hydrolysis in an amount of 1.5 mg to 15 mg protein/gram dry matter weight of glucans in the cellulosic material. In an embodiment the enzyme composition is used in the enzymatic hydrolysis in an amount of 2 mg to 12 mg protein/gram dry matter weight of glucans in the cellulosic material. In an embodiment the enzyme composition is used in the enzymatic hydrolysis in an amount of 2 mg to 10 mg protein/gram dry matter weight of glucans in the cellulosic material.

In an embodiment the fermentation (i.e. step b) is performed in one or more fermentation reactors. In an embodiment the fermentation is conducted with a microorganism that is able to ferment at least one C5 sugar. In an embodiment the fermentation is done by an alcohol producing microorganism to produce alcohol. In an embodiment the fermentation is done by an organic acid producing microorganism to produce an organic acid. The fermentation by an alcohol producing microorganism to produce alcohol can be done in the same fermentation reactor(s) wherein the enzymatic hydrolysis is performed. Alternatively, the fermentation by an alcohol producing microorganism to produce alcohol and the fermentation by an organic acid producing microorganism to produce an organic acid can be performed in one or more separate fermentation reactors but may also be done in one or more of the same fermentation reactors.

In an embodiment the fermentation is done by a yeast. In an embodiment the alcohol producing microorganism and/or the organic acid producing microorganism is a yeast. In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid.

In a further aspect, the present disclosure thus includes fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/I glucose and corresponding other sugars from the carbohydrate material (e.g. 50 g/I xylose, 35 g/I L-arabinose and 10 g/I galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem, many microorganisms use pyruvate or one of its derivatives as an electron and hydrogen acceptor thereby regenerating NAD⁺. Thus, in a preferred anaerobic fermentation process pyruvate is used as an electron (and hydrogen acceptor) and is reduced to fermentation products such as ethanol, lactic acid, 3-hydroxypropionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

In an embodiment the alcohol fermentation process is anaerobic, while the organic acid fermentation process is aerobic, but done under oxygen-limited conditions.

The fermentation process is preferably run at a temperature that is optimal for the microorganism used. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment, the fermentations are conducted with a fermenting microorganism. In an embodiment, the alcohol (e.g. ethanol) fermentations of C5 sugars are conducted with a C5 fermenting microorganism. In an embodiment, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Food Specialties), GERT STRAND™ (Gert Strand AB, Sweden), and SUPERSTART™ and THERMOSACC™ fresh yeast (Ethanol Technology, WI, USA).

In a preferred embodiment the fermentation product is alcohol and the fermenting microorganism is an alcohol producing microorganism that is able to ferment at least one C5 sugar.

In an embodiment propagation of the alcohol producing microorganism and/or the organic acid producing microorganism is performed in one or more propagation reactors. After propagation, the alcohol producing microorganism and/or the organic acid producing microorganism may be added to one or more fermentation reactors. Alternatively, the propagation of the alcohol producing microorganism and/or the organic acid producing microorganism is combined with the fermentation by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the present disclosure also describes a process for the preparation of ethanol from cellulosic material, comprising the steps of (a) performing a process for the preparation of a sugar product from cellulosic material as described herein, (b) fermentation of the enzymatically hydrolysed cellulosic material to produce ethanol; and (c) optionally, recovery of the ethanol. The fermentation can be done with a microorganism that is able to ferment at least one C5 sugar.

In an embodiment the organic acid producing microorganism is a microorganism that is able to ferment at least one C6 sugar. In an embodiment the present disclosure describes a process for the preparation of succinic acid from cellulosic material, comprising the steps of (a) performing a process for the preparation of a sugar product from cellulosic material as described herein, (b) fermentation of the enzymatically hydrolysed cellulosic material to produce succinic acid; and (c) optionally, recovery of the succinic acid. The fermentation can be done with a microorganism that is able to ferment at least one C6 sugar.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes as described herein is capable of converting hexose (C6) sugars and pentose (C5) sugars. The yeast, e.g. *Saccharomyces cerevisiae*, used in the processes as described herein can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/ or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

Alternatively, to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus, Byssochlamys nivea, Lentinus degener, Paecilomyces varioti* and *Penicillium viniferum*; and bacteria, for instance *Anaerobiospirillum succiniciproducens, Actinobacillus suc-*

*cinogenes, Mannhei succiniciproducers* MBEL 55E, *Escherichia coli, Propionibacterium species, Pectinatus* sp., *Bacteroides* sp., such as *Bacteroides amylophilus, Ruminococcus flavefaciens, Prevotella ruminicola, Succcinimonas amylolytica, Succinivibrio dextrinisolvens, Wolinella succinogenes*, and *Cytophaga succinicans*. In an embodiment the organic acid producing microorganism that is able to ferment at least one C6 sugar is a yeast. In an embodiment, the yeast belongs to the genus *Saccharomyces*, preferably of the species *Saccharomyces cerevisiae*. The yeast, e.g. *Saccharomyces cerevisiae*, used in the production processes of organic acid as described herein is capable of converting hexose (C6) sugars. The yeast, e.g. *Saccharomyces cerevisiae*, used in the processes as described herein can anaerobically ferment at least one C6 sugar.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products that may be produced by the processes as described herein can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an organic acid and/or an alcohol is prepared in the fermentation processes as described herein. In a preferred embodiment succinic acid and/or ethanol is prepared in the fermentation processes as described herein. Preferably, the fermentation product is alcohol, preferably ethanol.

The beneficial effects as described herein are found for several cellulosic materials and therefore believed to be present for the hydrolysis of all kind of cellulosic materials. The beneficial effects are found for several enzymes and therefore believed to be present for all kind of hydrolysing enzyme compositions.

In an embodiment the enzyme composition as used in the processes as described herein comprises at least a cellulase and/or at least a hemicellulase.

In an embodiment the enzyme composition as used in the processes as described herein is in the form of a whole fermentation broth of a fungus.

In an embodiment the enzyme composition as used in the processes as described herein comprises a beta-glucosidase (BG), an endoglucanase (EG), a lytic polysaccharide monooxygenase (LPMO), a cellobiohydrolase (CBH), a beta-xylosidase and an endoxylanase (EX).

Endoglucanases are enzymes which are capable of catalyzing the endohydrolysis of 1,4-β-D-glucosidic linkages in cellulose, lichenin or cereal β-D-glucans. They belong to EC 3.2.1.4 and may also be capable of hydrolyzing 1,4-linkages in β-D-glucans also containing 1,3-linkages. Endoglucanases may also be referred to as cellulases, avicelases, β-1,4-endoglucan hydrolases, β-1,4-glucanases, carboxymethyl cellulases, cellodextrins, endo-1,4-β-D-glucanases, endo-1,4-β-D-glucanohydrolases or endo-1,4-β-glucanases.

In an embodiment the endoglucanase comprises a GH5 endoglucanase and/or a GH7 endoglucanase. This means that at least one of the endoglucanases in the enzyme composition is a GH5 endoglucanase or a GH7 endoglucanase. In case there are more endoglucanases in the enzyme composition, these endoglucanases can be GH5 endoglucanases, GH7 endoglucanases or a combination of GH5 endoglucanases and GH7 endoglucanases. In a preferred embodiment the endoglucanase comprises a GH5 endoglucanase. GH classification can be found on the CAZy website.

In an embodiment the enzyme composition comprises an endoglucanase from *Trichoderma*, such as *Trichoderma reesei*; from *Aspergillus*, such as *Aspergillus aculeatus, Aspergillus terreus* or *Aspergillus kawachii*; from *Erwinia*, such as *Erwinia carotovora*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum*; and/or from *Chrysosporium*, such as a strain of *Chrysosporium lucknowense*. In an embodiment even a bacterial endoglucanase can be used including, but not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

In an embodiment the endoglucanase is a thermostable endoglucanase. A "thermostable" endoglucanase as used herein means that the endoglucanase has a temperature optimum in the range of 45° C. to 90° C. when activity is measured between 10-30 minutes. Thermostable endoglucanases may for example be isolated from thermophilic or thermotolerant fungi or may be designed by the skilled person and artificially synthesized. In one embodiment the thermostable endoglucanase may be isolated or obtained from thermophilic or thermotolerant filamentous fungi or isolated from non-thermophilic or non-thermotolerant fungi but are found to be thermostable. In an embodiment the thermostable endoglucanase is fungal. In an embodiment the thermostable endoglucanase is obtained from a thermophilic or thermotolerant fungus. By "thermophilic fungus" is meant a fungus that grows at a temperature of 45° C. or higher. By "thermotolerant" fungus is meant a fungus that grows at a temperature of 20° C. or higher, having a maximum near 55° C.

In an embodiment the thermostable endoglucanase is obtained from a fungus of the genus including, but not limited to, *Humicola, Rhizomucor, Myceliophthora, Rasamsonia, Talaromyces, Penicillium, Thermomyces, Thermoas

*cus, Aspergillus, Scytalidium, Paecilomyces, Chaetomium, Stibella, Corynascus, Malbranchea* or *Thielavia*. Preferred species of these genera include, but are not limited to, *Humicola grisea* var. *thermoidea, Humicola lanuginosa, Humicola hyalothermophilia, Myceliophthora thermophila, Myceliophthora hinnulea, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Talaromyces emersonii, Thermomyces lenuginosus, Thermomyces stellatus, Thermoascus crustaceus, Thermoascus thermophilus, Thermoascus aurantiacus, Penicillium emersonii, Penicillium cylindrosporum, Aspergillus terreus, Aspergillus fumigatus, Scytalidium thermophilum, Paecilomyces byssochlamydoides, Chaetomium thermophilum, Chaetomium olivicolor, Stibella thermophila, Corynascus sepedonium, Malbranchea cinnamonmea* and *Thielavia terrestris*.

In a preferred embodiment the thermostable endoglucanase is obtained from a fungus of the genus *Rasamsonia, Talaromyces, Thermoascus* or *Penicillium*.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalose, β-D-glucoside glucohydrolase, cellobiase or gentibiose.

In an embodiment the enzyme composition comprises a beta-glucosidase from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus* aculeatus, *Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/ 0258554 US 2004/0102619. In an embodiment even a bacterial beta-glucosidase can be used. In another embodiment the beta-glucosidase is derived from *Thielavia terrestris* (WO 2011/035029) or *Trichophaea saccata* (WO 2007/ 019442). In a preferred embodiment the enzyme composition comprises a beta-glucosidase from *Rasamsonia*, such as *Rasamsonia emersonii* (see WO 2012/000886 or WO 2012/000890).

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobioside, 1,4-β-cellobiohydrolase, 1,4-β-D-glucan cellobiohydrolase, avicelase, exo-1,4-β-D-glucanase, exocellobiohydrolase or exoglucanases.

In an embodiment the cellobiohydrolase is a cellobiohydrolase I such as a GH7 cellobiohydrolase I.

In a preferred embodiment the cellobiohydrolase I is obtained from a fungus of the genus *Rasamsonia, Talaromyces, Aspergillus, Trichoderma* or *Penicillium*. In a preferred embodiment the cellobiohydrolase I is obtained from a fungus of the species *Rasamsonia emersonii, Talaromyces emersonii, Talaromyces leycettanus, Aspergillus fumigatus, Trichoderma reesei* or *Penicillium emersonii*.

In an embodiment the enzyme composition comprises a cellobiohydrolase I from *Aspergillus*, such as *Aspergillus fumigatus*, such as the Cel7A CBHI disclosed in SEQ ID NO:6 in WO 2011/057140 or SEQ ID NO:6 in WO 2014/130812 or a CBHI such as disclosed in WO 2013/028928 or WO 2015/081139; from *Trichoderma*, such as *Trichoderma reesei*; from *Chaetomium*, such as *Chaetomium thermophilum*; from *Talaromyces*, such as *Talaromyces* leycettanus (e.g. such as disclosed in WO 2015/187935 or WO 2016/082771), or from *Penicillium*, such as *Penicillium emersonii* (e.g. such as disclosed in WO 2011/057140). In a preferred embodiment the enzyme composition comprises a cellobiohydrolase I from *Rasamsonia*, such as *Rasamsonia emersonii* (see WO 2010/122141).

In an embodiment the enzyme composition as used in the processes as described herein may comprise a hemicellulase. As described herein the enzyme composition of the present disclosure preferably comprises a hemicellulase. It is to be understood that "a hemicellulase" means "at least one hemicellulase". The enzyme composition of the present disclosure may thus comprise more than one hemicellulase. In an embodiment the hemicellulase comprises a beta-xylosidase and/or an endoxylanase.

As used herein, beta-xylosidases (EC 3.2.1.37) are polypeptides which are capable of catalysing the hydrolysis of 1,4-β-D-xylans, to remove successive D-xylose residues from the non-reducing termini. Beta-xylosidases may also hydrolyze xylobiose. Beta-xylosidase may also be referred to as xylan 1,4-β-xylosidase, 1,4-β-D-xylan xylohydrolase, exo-1,4-β-xylosidase or xylobiose.

In an embodiment the beta-xylosidase comprises a GH3 beta-xylosidase. This means that at least one of the beta-xylosidases in the enzyme composition is a GH3 beta-xylosidase. In an embodiment all beta-xylosidases in the enzyme composition are GH3 beta-xylosidases.

In an embodiment the enzyme composition comprises a beta-xylosidase from *Neurospora crassa, Aspergillus fumigatus* or *Trichoderma reesei*. In a preferred embodiment the enzyme composition comprises a beta-xylosidase from *Rasamsonia*, such as *Rasamsonia emersonii* (see WO 2014/118360).

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

In an embodiment the endoxylanase comprises a GH10 xylanase. This means that at least one of the endoxylanases in the enzyme composition is a GH10 xylanase. In an embodiment all endoxylanases in the enzyme composition are GH10 xylanases.

In an embodiment the enzyme composition comprises an endoxylanase from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), *Talaromyces leycettanus, Thermo-*

*bifida fusca*, or *Trichophaea saccata* GH10 (see WO 2011/057083). In a preferred embodiment the enzyme composition comprises an endoxylanase from *Rasamsonia*, such as *Rasamsonia emersonii* (see WO 02/24926).

As used herein, lytic polysaccharide monooxygenases are enzymes that have recently been classified by CAZy in family AA9 (Auxiliary Activity Family 9) or family AA10 (Auxiliary Activity Family 10). Ergo, there exist AA9 lytic polysaccharide monooxygenases and AA10 lytic polysaccharide monooxygenases. Lytic polysaccharide monooxygenases are able to open a crystalline glucan structure and enhance the action of cellulases on lignocellulose substrates. They are enzymes having cellulolytic enhancing activity. Lytic polysaccharide monooxygenases may also affect cellooligosaccharides. According to the latest literature, (see Isaksen et al., Journal of Biological Chemistry, vol. 289, no. 5, p. 2632-2642), proteins named GH61 (glycoside hydrolase family 61 or sometimes referred to EGIV) are lytic polysaccharide monooxygenases. GH61 was originally classified as endoglucanase based on measurement of very weak endo-1,4-β-d-glucanase activity in one family member but have recently been reclassified by CAZy in family AA9. CBM33 (family 33 carbohydrate-binding module) is also a lytic polysaccharide monooxygenase (see Isaksen et al, Journal of Biological Chemistry, vol. 289, no. 5, pp. 2632-2642). CAZy has recently reclassified CBM33 in the AA10 family.

In an embodiment the lytic polysaccharide monooxygenase comprises an AA9 lytic polysaccharide monooxygenase. This means that at least one of the lytic polysaccharide monooxygenases in the enzyme composition is an AA9 lytic polysaccharide monooxygenase. In an embodiment, all lytic polysaccharide monooxygenases in the enzyme composition are AA9 lytic polysaccharide monooxygenase.

In an embodiment the enzyme composition comprises a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus* crustaceous (see WO 2011/041504). Other cellulolytic enzymes that may be comprised in the enzyme composition are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648, 263, and 5,686,593, to name just a few. In a preferred embodiment, the lytic polysaccharide monooxygenase is from *Rasamsonia*, e.g. *Rasamsonia emersonii* (see WO 2012/000892).

In an embodiment the enzyme composition comprises a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In a preferred embodiment the enzyme composition comprises a cellobiohydrolase II from *Rasamsonia*, such as *Rasamsonia emersonii* (see WO 2011/098580).

An enzyme composition comprises preferably at least two activities, although typically a composition will comprise more than two activities, for example, three, four, five, six, seven, eight, nine or even more activities. An enzyme composition may comprise more than one enzyme activity per activity class. An enzyme composition may comprise one type of cellulase activity and/or hemicellulase activity and/or pectinase activity.

In an embodiment the enzyme composition comprises at least two cellulases. As used herein, a cellulase is any polypeptide which is capable of degrading or modifying cellulose. The at least two cellulases may contain the same or different activities. The enzyme composition may also comprise at least one enzyme other than a cellulase, e.g. a hemicellulase or a pectinase. As used herein, a hemicellulase is any polypeptide which is capable of degrading or modifying hemicellulose. As used herein, a pectinase is any polypeptide which is capable of degrading or modifying pectin. The at least one other enzyme may have an auxiliary enzyme activity, i.e. an additional activity which, either directly or indirectly leads to lignocellulose degradation. Examples of such auxiliary activities are mentioned herein.

In an embodiment the enzyme composition as described herein comprises one, two, three, four classes or more of cellulase, for example one, two, three or four or all of an endoglucanase, a lytic polysaccharide monooxygenase, a cellobiohydrolase I, a cellobiohydrolase II and a beta-glucosidase.

In an embodiment the enzyme composition as used in the processes as described herein comprises an endoglucanase, a cellobiohydrolase I, a lytic polysaccharide monooxygenase, a cellobiohydrolase II, a beta-glucosidase, a beta-xylosidase and an endoxylanase.

In an embodiment the enzyme composition also comprises one or more of the below mentioned enzymes.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as lichenase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanase when the glucose residue whose reducing group is involved in the linkage to be hydrolysed is itself substituted at C-3. Alternative names include endo-1,3-beta-glucanase, laminarinase, 1,3-(1,3; 1,4)-beta-D-glucan 3 (4) glucanohydrolase. Substrates include laminarin, lichenin and cereal beta-D-glucans.

As used herein, an α-L-arabinofuranosidase (EC 3.2.1.55) is any polypeptide which is capable of acting on α-L-arabinofuranoside, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidases. Examples of arabinofuranosidases that may be comprised in the enzyme composition include, but are not limited to, arabinofuranosidases from *Aspergillus niger*, *Humicola insolens* DSM 1800 (see WO 2006/114094 and WO 2009/073383) and *M. giganteus* (see WO 2006/114094).

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronidase, which catalyses the hydrolysis of alpha-1,2-(4-O-methyl) glucuronosyl links. Examples of alpha-glucuronidases that may be comprised in the enzyme composition include, but are not limited to, alpha-glucuronidases from *Aspergillus clavatus*, *Aspergillus* fumigatus, *Aspergillus* niger, *Aspergillus terreus*, *Humicola insolens* (see WO 2010/014706), *Penicillium aurantiogriseum* (see WO 2009/068565) and *Trichoderma reesei*.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin. Examples of acetylxylan esterases that may be comprised in the enzyme composition include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). In a preferred embodiment the enzyme composition comprises an acetyl xylan esterase from *Rasamsonia*, such as *Rasamsonia emersonii* (see WO 2010/000888)

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin. Examples of feruloyl esterases (ferulic acid esterases) that may be comprised in the enzyme composition include, but are not limited to, feruloyl esterases form *Humicola insolens* DSM 1800 (see WO 2009/076122), Neosartorya *fischeri, Neurospora crassa, Penicillium aurantiogriseum* (see WO 2009/127729), and *Thielavia terrestris* (see WO 2010/053838 and WO 2010/065448).

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosidase. This enzyme may also be referred to as melibiose.

As used herein, a p-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolyase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n $H_2O$=n methanol+pectate. The enzyme may also be known as pectinesterase, pectin demethylase, pectin methoxylase, pectin methylesterase, pectase, pectinesterases or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transleliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnoside or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonisidases, exopolygalacturonosidase or exopolygalacturanosidase.

As used herein, exo-galacturonase (EC 3.2.1.67) is any polypeptide capable of catalysing: (1,4-α-D-galacturonide)$_n$+$H_2O$=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L- arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanases (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin.

Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used is a ß-glucano-syltransferase. Such an enzyme may be able to catalyze degradation of (1,3)(1,4)glucan and/or cellulose and/or a cellulose degradation product.

"Glucuronidase" includes enzymes that catalyze the hydrolysis of a glucuronoside, for example β-glucuronoside to yield an alcohol. Many glucuronidases have been characterized and may be suitable for use, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. As described herein, an expansin-like protein or swollenin-like protein may comprise one or both of such domains and/or may disrupt the structure of cell walls (such as disrupting cellulose structure), optionally without producing detectable amounts of reducing sugars.

A cellulose induced protein, for example the polypeptide product of the cip1 or cip2 gene or similar genes (see Foreman et al., J. Biol. Chem. 278(34), 31988-31997, 2003), a cellulose/cellulosum integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosum to its substrate. A scaffoldin or cellulose integrating protein may comprise one or both of such domains.

A catalase; the term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextrinase (EC 3.2.1.142).

As used herein, glucoamylases (EC 3.2.1.3) are exoglucohydrolases that catalyse hydrolysis of α-1,4 and α-1,6 glucosidic linkages to release β-D-glucose from the non-reducing ends of starch and related poly- and oligosaccharides. They are also called amyloglucosidase, glucan 1,4-alpha-glucosidase or 1,4-alpha-D-glucan glucohydrolase. They catalyzes the release of D-glucose from the non-reducing ends of starch or related oligo- and polysaccharide molecules. The majority of glucoamylases are multidomain enzymes consisting of a catalytic domain connected to a starch binding domain by an O-glycosylated linker region of varying lengths. As used herein, glucoamylases also include alpha-glycosidases (EC 3.2.1.20). The glucoamylase may be a GH15 glucoamylase, a GH31 glucoamylase, a GH97 glucoamylase or any combination thereof. The enzyme composition as described herein may comprise a glucoamylase. The glucoamylase as used herein belongs to the structural family GH15, GH31 or GH97. The glucoamylase may be a fungal glucoamylase. The glucoamylase may be a glucoamylase from *Aspergillus, Trichoderma, Rasamsonia, Penicillium, Rhizopus, Thermomyces*, to name just a few.

The glucoamylase may also be an engineered glucoamylase, such as a variant enzyme comprising one or more mutations, deletions and/or insertions.

An enzyme composition may be composed of a member of each of the classes of enzymes mentioned above, several members of one enzyme class, or any combination of these enzyme classes. Different enzymes in an enzyme composition as described herein may be obtained from different sources.

In the uses and processes described herein, the components of the compositions described above may be provided concomitantly (i.e. as a single composition per se) or separately or sequentially.

In an embodiment the enzymes in the enzyme composition are derived from a fungus, preferably a filamentous fungus or the enzymes comprise a fungal enzyme, preferably a filamentous fungal enzyme. In an embodiment a core set of (ligno)cellulose degrading enzymes (i.e. cellulases and/or a hemicellulases and/or a pectinases) may be derived from *Rasamsonia emersonii*. If needed, the set of enzymes can be supplemented with additional enzyme activities from other sources. Such additional activities may be derived from classical sources and/or produced by genetically modified organisms. Thus, the enzyme composition may comprise a cellulase and/or a hemicellulase and/or a pectinase from a source other than *Rasamsonia*. In an embodiment they may be used together with one or more *Rasamsonia* enzymes or they may be used without additional *Rasamsonia* enzymes being present.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes, Trichoderma* and *Trichophyton*.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *Penicillium chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae*

ATCC11906, *Chrysosporium lucknowense* C1, Garg 27K, VKM F-3500-D, ATCC44006 and derivatives thereof.

The enzymes (for example in the form of a whole fermentation broth) may be prepared by fermentation of a suitable substrate with a suitable microorganism, e.g. a filamentous fungus, wherein the enzymes are produced by the microorganism. The microorganism may be altered to improve or to make the enzymes. For example, the microorganism may be mutated by classical strain improvement procedures or by recombinant DNA techniques. Therefore, the microorganisms mentioned herein can be used as such to produce the enzymes or may be altered to increase the production or to produce altered enzymes, which might include heterologous enzymes, e.g. cellulases and/or hemicellulases and/or pectinases, thus enzymes that are not originally produced by that microorganism. Preferably, a fungus, more preferably a filamentous fungus, is used to produce the enzymes. Advantageously, a thermophilic or thermotolerant microorganism is used. Optionally, a substrate is used that induces the expression of the enzymes by the enzyme producing microorganism.

In an embodiment the enzyme composition is a whole fermentation broth. In an embodiment the enzyme composition is a whole fermentation broth of a fungus, preferably a filamentous fungus, preferably of the genus *Rasamsonia*. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus, wherein the one or more genes encode enzymes that can degrade a cellulosic substrate. The whole fermentation broth may comprise any of the polypeptides described herein or any combination thereof.

Preferably, the enzyme composition is a whole fermentation broth, wherein cells are killed, i.e. nonviable. In an embodiment the whole fermentation broth comprises polypeptides, organic acid(s), killed cells and/or cell debris, and culture medium.

Generally, the filamentous fungi are cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth may comprise filamentous fungi. In an embodiment, the whole fermentation broth comprises the unfractionated contents of the fermentation materials derived at the end of the fermentation. Typically, the whole fermentation broth comprises the spent culture medium and cell debris present after the filamentous fungi are grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. The filamentous fungal cells present in whole fermentation broth can be killed using methods known in the art to produce a cell-killed whole fermentation broth. For instance, addition of organic acid leads to killing of the cells. If needed, the cells may also be lysed and/or permeabilized. In an embodiment, the whole fermentation broth is a cell-killed whole fermentation broth, wherein the whole fermentation broth containing the filamentous fungal cells are killed. In other words, the whole fermentation broth comprises more nonviable cells than viable cells, preferably only nonviable cells. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth is mixed with an organic acid.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably nonviable, cells.

In an embodiment the whole fermentation broth can be fractionated and the one or more of the fractionated contents can be used. For instance, the killed cells and/or cell debris can be removed from a whole fermentation broth to provide an enzyme composition that is free of these components.

The whole fermentation broth may further comprise a preservative and/or anti-microbial agent. Such preservatives and/or agents are known in the art. In an embodiment the organic acid used for killing the cells can also have the function of preservative and/or anti-microbial agent.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously or expressed at relatively low level by the filamentous fungi, to improve the degradation of the cellulosic substrate, for example, to fermentable sugars such as glucose or xylose. The supplemental enzyme(s) can be added as a supplement to the whole fermentation broth, i.e. they are spiked to the whole fermentation broth. The additional enzymes may be supplemented in the form of a whole fermentation broth, or may be supplemented as purified, or minimally recovered and/or purified, enzymes.

In an embodiment, the whole fermentation broth may be supplemented with at least another whole fermentation broth. The other whole fermentation broth may be derived from the same type of fungus or from another type of fungus, e.g. a first whole fermentation broth may be derived from *Rasamsonia*, while a second whole fermentation broth may be derived from *Rasamsonia* or *Aspergillus*.

In an embodiment, the whole fermentation broth is a whole fermentation broth of a fermentation of a recombinant filamentous fungus overexpressing one or more enzymes to improve the degradation of the cellulosic substrate. Alternatively, the whole fermentation broth is a mixture of a whole fermentation broth of a fermentation of a non-recombinant filamentous fungus and a whole fermentation broth of a recombinant filamentous fungus overexpressing one or more enzymes to improve the degradation of the cellulosic substrate. In an embodiment, the whole fermentation broth is a whole fermentation broth of a fermentation of a filamentous fungus overexpressing beta-glucosidase. Alternatively, the whole fermentation broth is a mixture of a whole fermentation broth of a fermentation of a non-recombinant filamentous fungus and a whole fermentation broth of a fermentation of a recombinant filamentous fungus overexpressing a beta-glucosidase.

In an embodiment the enzyme composition as described herein has a pH of 2.0 to 5.5. Preferably, the enzyme composition has a pH of 2.5 to 5.0. More preferably, the enzyme composition has a pH of 3.0 to 4.5. Ergo, the enzymes in the enzyme composition are able to work at low pH.

In an embodiment the enzyme production reactor(s) used in the process for the preparation of an enzyme composition as described herein have a volume of at least 1 m³. Preferably, the enzyme production reactors have a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³. In general, the enzyme production reactor(s) will be smaller than 300 m³.

In the process for the preparation of an enzyme composition as described herein, a population of microbial cells, e.g. filamentous fungal cells, is cultured under suitable conditions for growth, in a liquid or solid medium. In an embodiment the microbial cells are cultured in a fed-batch culture, a batch culture, a continuous culture or any combination thereof. Preferably, the filamentous fungus is cultured in a fed-batch culture. A person skilled in the art is well aware of the various modes of culturing and its conditions. In an embodiment the culturing is conducted under aerobic conditions. A person skilled in the art is well aware of fermentor designs for aerobic cultivation such as for instance stirred tanks and bubble columns.

EXAMPLES

Example 1

Xylonic Acid Production During Enzymatic Hydrolysis of Cellulosic Material

The enzymatic hydrolysis was performed using acid-pretreated corn stover at a concentration of 15% (w/w) dry matter. The acid-pretreated corn stover contained 13% (w/w) total xylan on dry matter (including insoluble xylan, soluble xylooligomers and xylose). The pretreated corn stover was diluted with water and the pH was adjusted to pH 4.5 with a 10% (w/w) NH₄OH-solution. The enzymatic hydrolysis was performed at 1 kg scale using 1.5 liter reactors. The pH was controlled at 4.5 and the temperature during enzymatic hydrolysis was controlled at 62° C.

TEC-210 was produced according to the inoculation and fermentation procedures described in WO 2011/000949.

The protein concentration of the TEC210 cellulase cocktail sample was determined using a Biuret method. In the Biuret reaction, a copper(II) ion is reduced to copper(I), which forms a complex with the nitrogens and carbons of the peptide bonds in an alkaline solution. A violet color indicates the presence of protein. The intensity of the color, and hence the absorption at 546 nm, is directly proportional to the protein concentration, according to the Lambert-Beer law. Peptides also respond in this assay, they are excluded by performing a 10 kD filtration on the samples and subtracting the result of this 10 kD filtrate from the 'as such' samples.

Bovine serum albumin (BSA) dilutions (0.5, 1, 2, 5, 10 and 15 mg/ml) were made with water, containing 0.2 g/L Tween 80, to generate a calibration curve. The TEC210 cellulase cocktail samples were appropriately diluted, to fall within the result of the BSA calibration line, on weight basis with water and centrifuged for 5 minutes at >14000×g. The supernatant of each diluted sample was collected and further referred to as Sample-supernatants. Next, 500 μL of the Sample-supernatants of each diluted sample was transferred to a centrifugal reaction tube containing a 10 kD filter and centrifuged as long as needed between 15-20° C. to obtain at least 200 μL of filtrate, further referred to as Sample-supernatants-10 kD filtrate.

From all Sample-supernatants, Sample-supernatants-10 kD filtrate and BSA dilutions, 200 μL was transferred into a 1.5 mL reaction tube, to which 800 μL BioQuant Biuret reagent was added and mixed thoroughly. Next, all the mixtures were incubated at room temperature for at least 30 minutes. The absorption of the mixtures was measured at 546 nm with a water sample used as a blank measurement. Dilutions of the TEC-210 cellulase cocktail samples that gave an absorption value at 546 nm within the range of the BSA calibration line were used to calculate the total protein concentration of the samples via the BSA calibration line. The protein concentrations measured in the Sample-supernatants-10 kD filtrate where subtracted from the protein concentrations measured in the Sample-supernatants to get to a final protein concentration in TEC-210 cellulase cocktail sample.

Next, the cellulase enzyme cocktail TEC210 was added to the pretreated corn stover at a dosage of 2.5 mg (protein)/g dry matter. All reactors were operated for the first 6 hours at a stirrer speed of 150 rpm under a nitrogen blanket to liquefy the viscous feedstock (headspace of the reactors was continuously flushed with nitrogen at a rate of 100 mL/min). After 6 hours, the nitrogen flow was replaced by an air flow (100 mL/min) and the hydrolysis continued for 66 hours, resulting in total hydrolysis time of 72 hours.

The oxygen concentration in the reaction mixture was controlled by the stirrer speed (this gave control over the introduction of oxygen from the headspace of the reactor into the reaction mixture). The headspace of the reactors was continuously supplied with fresh air (containing 20-21% oxygen) to secure the presence of sufficient oxygen in the headspace. The stirrer speeds in the different reactors were 100-120-140-170-200 rpm. The estimated oxygen concentration during enzymatic hydrolysis corresponding with these stirrer speed values were 100 rpm (0.0002-0.002 mol $O_2/m^3$)-120 rpm (0.002-0.016 mol $O_2/m^3$)-140 rpm (0.016-0.047 mol $O2/m^3$)-170 rpm (0.047-0.078 mol $O2/m^3$)-200 rpm (0.078-0.109 mol $O2/m^3$), wherein oxygen concentrations were not measured but estimated based on previous experiments.

A control experiment was conducted at a stirrer speed of 150 rpm under a nitrogen blanket to exclude oxygen as much as possible.

Time samples were drawn during the experiments to measure glucose and xylonic acid amounts. The samples were immediately centrifuged for 8 minutes at 4000×g. The supernatant was filtered over 0.20 μm nylon filters and the filtrates were stored at 4° C. until analysis. The glucose concentration of the samples was measured using an HPLC equipped with an Aminex HPX-87H column according to the NREL technical report NREL/TP-510-42623, January 2008.

Quantification of xylonic acid was performed with an ICS3000 dual LC system (Thermo Fisher) equipped with an IonPac AS11-HC column (2.0×250 mm) (Thermo Fisher), with IonPac AG11-HC guard column (2×50 mm) (Thermo Fisher), using a gradient elution with (A) Milli-Q purified water, and (B) 5 mM NaOH, (C) 100 mM NaOH as mobile phases. The gradient started with 80% A and 20% B for 8 minutes, followed by a linear increase to 85% A and 15% C in 10 minutes, and a linear increase to 70% A and 30% C in 10 minutes. Subsequently, the gradient went back to the starting condition within 1 minute, and equilibrated for 10 minutes. The flow-rate was kept at 0.38 ml/min, using an injection volume of 25 μl and the column temperature was set to 30° C. Detection was performed with suppressed conductivity and xylonic acid eluted at tr=7.0 min.

Xylonic acid concentration was determined using D-xylonic acid calcium salt (Santa Cruz Biotechnology) and external calibration. The amount of xylonic acid produced during aeration was calculated by subtracting the concentration measured at t=6 hours from the concentration measured at t=72 hours. The production speed was then calculated by dividing the xylonic acid amount produced by the hours it took to produce this amount, i.e. 66 hours (72 h-6 h) and expressing this in μmol xylonic acid produced per Liter hydrolysate per hour (μmol/L/h). Next, the amount of xylonic acid produced in μmol/kg xylan in 1 hour was calculated as follows:

$$\text{Xylonic acid}(\mu mol/L/h) \times (\text{pellet factor/density})/\text{xylan} \text{ (kg/kg hydrolysate)}$$

wherein the pellet factor used was 0.947, density 1.044 kg/L and xylan of 0.019 kg/kg hydrolysate of 15% dry matter.

The results are presented in Table 1 and clearly show that a high glucose release is obtained when 500-1100 μmol xylonic acid/kg xylan per hour is produced during oxygen addition.

TABLE 1

| Glucose release after 72 hours and xylonic acid production speed in an enzymatic hydrolysis process of cellulosic material. | | | | |
|---|---|---|---|---|
| Stirrer speed (rpm) | Glucose (g/l) | Xylonic acid produced (g/l) | Xylonic acid production speed (μmol/kg hydrolysate · hour) | Xylonic acid production speed (μmol/kg xylan · hour) |
| Control | 29.4 | 0.075 | 7.0 | 370 |
| 100 | 39.6 | 0.125 | 10.3 | 544 |
| 120 | 40.5 | 0.185 | 15.3 | 806 |
| 140 | 38.9 | 0.245 | 20.3 | 1067 |
| 170 | 36.1 | 0.255 | 21.1 | 1110 |
| 200 | 35.2 | 0.285 | 23.6 | 1241 |

The invention claimed is:

1. Process for the preparation of a sugar product from cellulosic material, comprising the following steps:
    a) enzymatic hydrolysis of the cellulosic material using an enzyme composition to obtain the sugar product, wherein oxygen is added to maintain an oxygen concentration during enzymatic hydrolysis of i. 0.0002-0.002 mol $O^2/m^3$ when the reactor stirrer speed is 100 rpm;

ii. 0.002-0.016 mol $O^2/m^3$ when the reactor stirrer speed is 120 rpm;

iii. 0.016-0.047 mol $O^2/m^3$ when the reactor stirrer speed is 140 rpm;

so that xylonic acid is formed in an amount of 500 to 1100 μmol xylonic acid/kg xylan in the cellulosic material per hour, and b) recovery of the sugar product.

2. Process for the preparation of a fermentation product from cellulosic material, comprising the following steps:

a) enzymatic hydrolysis of the cellulosic material using an enzyme composition to obtain a sugar product, wherein oxygen is added to maintain an oxygen concentration during enzymatic hydrolysis of i. 0.0002-0.002 mol $O^2/m^3$ when the reactor stirrer speed is 100 rpm;

ii. 0.002-0.016 mol $O^2/m^3$ when the reactor stirrer speed is 120 rpm;

iii. 0.016-0.047 mol $O^2/m^3$ when the reactor stirrer speed is 140 rpm;

so that the xylonic acid is formed in an amount of 500 to 1100 μmol xylonic acid/kg xylan in the cellulosic material per hour, b) fermentation of the hydrolysed cellulosic material to produce a fermentation product, and c) recovery of the fermentation product.

3. Process according to claim 1, wherein the cellulosic material is pretreated before enzymatic hydrolysis.

4. Process according to claim 1, wherein the dry matter content in the enzymatic hydrolysis is from 10% to 40% (w/w).

5. A process according to claim 1, wherein the enzyme composition is in the form of a whole fermentation broth of a fungus.

6. Process according to claim 1, wherein the reactor for the enzymatic hydrolysis has a volume of 1 $m^3$ or more.

7. Process according to claim 1, wherein the reactor for the enzymatic hydrolysis has a volume of 50 $m^3$ or more.

8. Process according to claim 1, wherein the enzymatic hydrolysis is conducted at a temperature of from 50° C. to 70° C.

9. A process according to claim 1, wherein the enzymatic hydrolysis takes place in a batch, fed batch and/or continuous culture reactor.

10. A process according to claim 1, wherein oxygen is added to maintain an oxygen concentration of 0.0002-0.047 mol $O_2/m^3$ during enzymatic hydrolysis.

11. A process according to claim 1, wherein the enzyme composition comprises at least a cellulase and/or at least a hemicellulase.

12. A process according to claim 1, wherein the enzyme composition comprises a beta-glucosidase (BG), an endo-glucanase (EG), a lytic polysaccharide monooxygenase (LPMO), a cellobiohydrolase (CBH), a beta-xylosidase and an endoxylanase (EX).

13. Process according to claim 2, wherein the fermentation is conducted with a microorganism that is able to ferment at least one C5 sugar.

* * * * *